United States Patent [19]
O'Lenick, Jr.

[11] Patent Number: 5,919,959
[45] Date of Patent: Jul. 6, 1999

[54] GUERBET BRANCHED AMINE OXIDES

[75] Inventor: Anthony J. O'Lenick, Jr., Lilburn, Ga.

[73] Assignee: Lambent Tech Inc, Norcross, Ga.

[21] Appl. No.: 09/099,806

[22] Filed: Jun. 18, 1998

[51] Int. Cl.⁶ .................................................. C07C 235/00
[52] U.S. Cl. ................................................. 554/55; 554/51
[58] Field of Search ........................................ 554/51, 55

[56] References Cited

U.S. PATENT DOCUMENTS 5,488,121   1/1996   O'Lenick, Jr. .

*Primary Examiner*—Deborah D. Carr

[57] ABSTRACT

The present invention deals with the composition of matter and the utilization of certain novel guerbet based amine oxide compounds. These materials are useful in personal care applications.

11 Claims, No Drawings

GUERBET BRANCHED AMINE OXIDES

BACKGROUND OF THE INVENTION

1. Field of the Invention

The present invention deals with novel, surfactants, specifically amine oxides, based upon highly branched guerbet acids.

2. Description of the Art Practices

Guerbet alcohols have been known for many years. Over the years there have been a number of derivatives patented. These materials can be oxidized into acids, which are raw materials for the preparation of the specific complex esters of the present invention. They possess the critical regiospecific guerbet linkage which when placed into amidoamine compounds and amine oxides derived therefrom result in unexpected improvements in both liquidity oxidative stability.

U.S. Pat. No. 5,488,121 to O'Lenick, incorporated herein by reference, discloses di-guerbet esters based upon the reaction product of both a guerbet acid and a guerbet alcohol. The guerbet acids of that invention are raw materials used in the preparation of the compounds of the present invention.

1. Field of the Invention

The present invention deals with novel surfactants based upon a highly branched guerbet acid. The introduction of the guerbet branch into the amine oxide of the present invention results in improved conditioning and foam in personal care formulations as well as improved odor stability in the formulation and improved liquidity of the aqueous quat per se.

2. Description of the Art Practices

Amine oxides are known in the art. Variation of carbon chain lengths in amido amine oxides has direct effect upon the surfactant properties of the amine oxide. While amine oxides based upon short chain fatty acids can be made, they are poor surfactants. They lack conditioning effects on hair and do not give much foam to aqueous solutions. The use of fatty acids having more that 12 carbon atoms to make amine oxides result in amine oxides which provide little foam in aqueous systems, but have little or no conditioning effects. The selection of a oleyl amine oxides gives some improved viscosity, but the compound undergoes a process of oxidative instability referred to as rancidity, producing low molecular weight aldehydes with mal odor. The availability of a liquid, oxidatively stable amine oxide that can be used in personal care systems has been elusive prior to the compounds of the present invention.

The recent availability of guerbet acids and their reaction to make amine oxides results in the preparation liquid, high foaming, stable amine oxides, having outstanding emulsifying properties and are very acceptable for use in personal care applications.

None of the prior amine oxides possess the critical guerbet moiety. Molecules of the current invention have the guerbet group in the amine oxide.

THE INVENTION

This invention relates to the use of a guerbet acid to make an guerbet alkyl amidopropyl dialkyl amine oxide, which has unique, unexpected properties in personal care applications. Specifically, the amine oxides of the present invention provide a smooth feel on the skin, outstanding viscosity in anionic systems, and are surprisingly oxidatively stable in aqueous personal care formulations.

Another aspect of the present invention is the guerbet amidopropyl dialkyl amine intermediate useful as an intermediate in the preparation of the amine oxide of the present invention and other surfactant derivatives.

The compounds of the current invention are amine oxides derived from guerbet acid and conform to the following structure;

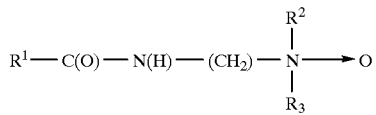

wherein:
$R^1$ is

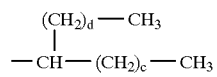

c and d are independently integers ranging from 3 to 17;
$R^2$ and $R^3$ are methyl or ethyl.

The amine oxide is prepared in a two step reaction. The first step is the preparation of a guerbet amidoamine conforming to the following structure:

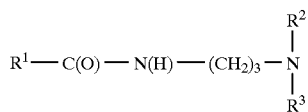

wherein:
$R^1$ is

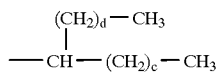

c and d are independently integers ranging from 3 to 17.

The reaction is as follows:

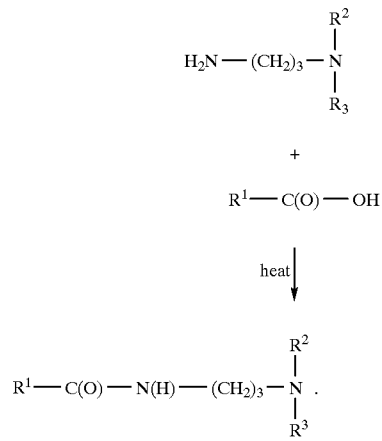

In the second reaction the amidoamine, prepared in the first reaction, is reacted in aqueous solution with of hydrogen peroxide as follows:

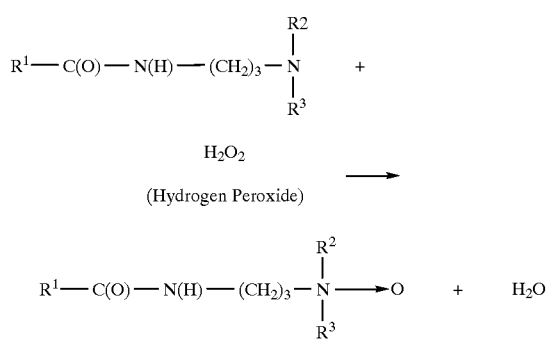

The hydrogen peroxide oxidizes the amine to the oxide and the by-product is water.

The concentration of the amine oxide in water is generally between 20 and 50% with 35% being preferred. Glycols, lower alcohols and other polar solvents may also be added, if desired.

EXAMPLES

Raw Materials

Guerbet Acids

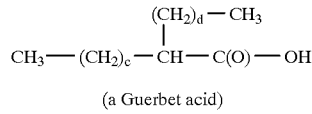

(a Guerbet acid)

Vista Chemical practices the oxidation of guerbet alcohols commercially. The values of c and d were actually determined by analysis and are not dependant upon trade name for meaning.

| Example | Commercial Name | c | d |
|---------|-----------------|----|----|
| 1 | Isocarb 10 | 3 | 3 |
| 2 | Isocarb 12 | 4 | 4 |
| 3 | Isocarb 14 | 5 | 5 |
| 4 | Isocarb 16 | 6 | 6 |
| 5 | Isocarb 18 | 7 | 7 |
| 6 | Isocarb 20 | 8 | 8 |
| 7 | Isocarb 32 | 14 | 14 |
| 8 | Isocarb 40 | 17 | 17 |

Isocarb is a trademark of Vista.

Aminopropyl Amine

The compounds conform to the following structure:

Example 9

Dimethyl Aminopropyl Amine

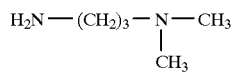

Example 10

Diethyl Aminopropyl Amine

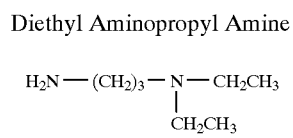

General Procedure

To the specified number of grams the specified dialkyl aminopropyl amine (Examples 9 and 10) is added the specified number of grams of the specified guerbet acid (examples 1–9) under agitation. The temperature of the mass is raised to 180–200 C. and water is stripped off as formed. This temperature is held for between 1 and 12 hours. The acid value and the primary amine value drops to vanishingly small levels and the tertiary amine level approaches theoretical.

The products are clear liquids and are liquid to extradorinary temperatures.

| Example | Guerbet Acid Example | Grams | Aminopropyl Amine Example | Grams |
|---------|---------|-------|---------|-------|
| 11 | 1 | 171.0 | 9 | 122.0 |
| 12 | 2 | 199.0 | 9 | 122.0 |
| 13 | 3 | 227.0 | 9 | 122.0 |
| 14 | 4 | 255.0 | 9 | 122.0 |
| 15 | 5 | 283.0 | 9 | 122.0 |
| 16 | 6 | 311.0 | 9 | 122.0 |
| 17 | 7 | 479.0 | 9 | 122.0 |
| 18 | 8 | 592.0 | 9 | 122.0 |
| 19 | 1 | 171.0 | 10 | 150.0 |
| 20 | 2 | 199.0 | 10 | 150.0 |
| 21 | 3 | 227.0 | 10 | 150.0 |
| 22 | 4 | 255.0 | 10 | 150.0 |
| 23 | 5 | 283.0 | 10 | 150.0 |
| 24 | 6 | 311.0 | 10 | 150.0 |
| 25 | 7 | 479.0 | 10 | 150.0 |
| 26 | 8 | 592.0 | 10 | 150.0 |

The compounds are the intermediate conforming to the following structure:

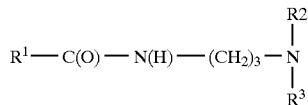

Hydrogen Peroxide

Hydrogen peroxide is an item of commerce and is available as a 50% by weight active material in water.

Amine Oxide Synthesis

To the specified 64.0 grams of 50% $H_2O_2$ is added to the specified amount of water. The solution is heated to 80 C. and the amidoamine (examples 11–26) is added under agitation. The pH is kept between 8–9 by adding NaOH as required.

Example 27

64.0 grams of 50% peroxide is added to 520 grams of water. The solution is heated to 80 C. and 438.0 grams of amidoamine (example 11) is added under agitation. The pH is kept between 8–9 by adding NaOH as required.

Example 28–42

Example 27 is repeated, only this time the specified amount of the specified amidoamine is added, replacing the amount used in example 27 and the specified amount of water is added, replacing the amount specified in example 27.

Examples 28–42

Example 27 is repeated, only this time the specified amount and type of amido amine is substituted for the amido amine of example 27.

| Example | Amidoamine Example | Grams |
|---------|---------|-------|
| 28 | 12 | 321.0 |
| 29 | 13 | 349.0 |
| 30 | 14 | 377.0 |
| 31 | 15 | 405.0 |
| 32 | 16 | 433.0 |
| 33 | 17 | 601.0 |
| 34 | 18 | 714.0 |
| 35 | 19 | 320.0 |
| 36 | 20 | 351.0 |
| 37 | 21 | 399.0 |
| 38 | 22 | 407.0 |
| 39 | 23 | 435.0 |
| 40 | 24 | 470.0 |
| 41 | 25 | 631.0 |
| 42 | 26 | 743.0 |

The products produced using the examples 27–42 are clear yellow viscous liquids. The products have outstanding oxidative stability and provide conditioning when applied ot the hair. In addition they are not irritating to the skin or eye.

I claim:

1. A guerbet amine oxide which conforms to the following structure:

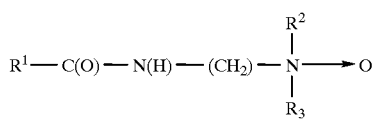

wherein:

$R^1$ is

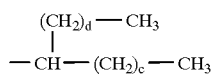

c and d are independently integers ranging from 3 to 17, $R^2$ and $R^3$ are methyl or ethyl.

2. A guerbet amine oxide of claim 1 wherein $R^2$ is methyl.

3. A guerbet amine oxide of claim 1 wherein $R^2$ is ethyl.

4. A guerbet amine oxide of claim 1 wherein c is 3 and d is 3.

5. A guerbet amine oxide of claim 1 wherein c is 4 and d is 4.

6. A guerbet amine oxide of claim 1 wherein c is 5 and d is 5.

7. A guerbet amine oxide of claim 1 wherein c is 6 and d is 6.

8. A guerbet amine oxide of claim 1 wherein c is 7 and d is 7.

9. A guerbet amine oxide of claim 1 wherein c is 8 and d is 8.

10. A guerbet amine oxide of claim 1 wherein c is 14 and d is 14.

11. A guerbet amine oxide of claim 1 wherein c is 17 and d is 17.

* * * * *